US012702284B2

(12) United States Patent
Tesar et al.

(10) Patent No.: US 12,702,284 B2
(45) Date of Patent: Aug. 11, 2026

(54) IMAGING SPECULUM FOR OTOLOGY

(71) Applicant: INFINITY RESEARCH INC., Germantown, TN (US)

(72) Inventors: John Tesar, Tucson, AZ (US); Steve Charles, Germantown, TN (US)

(73) Assignee: INFINITY RESEARCH INC., Germantown, TN (US)

(*) Notice: Subject to any disclaimer, the term of this patent is extended or adjusted under 35 U.S.C. 154(b) by 327 days.

(21) Appl. No.: 17/975,477

(22) Filed: Oct. 27, 2022

(65) Prior Publication Data

US 2023/0136044 A1 May 4, 2023

Related U.S. Application Data

(60) Provisional application No. 63/273,791, filed on Oct. 29, 2021.

(51) Int. Cl.

*A61B 1/227* (2006.01)
*A61B 1/00* (2006.01)
*A61B 1/05* (2006.01)

(52) U.S. Cl.

CPC .......... *A61B 1/227* (2013.01); *A61B 1/00147* (2013.01); *A61B 1/05* (2013.01)

(58) Field of Classification Search

CPC ................ A61B 1/227–2275; A61B 1/05–053
See application file for complete search history.

(56) References Cited

U.S. PATENT DOCUMENTS 5,785,648 A * 7/1998 Min .......................... A61B 1/32 600/206
6,616,603 B1 * 9/2003 Fontana ............... A61B 1/0623 600/184
7,762,949 B2 * 7/2010 Nakao ................ A61B 1/00073 600/125
10,368,733 B2 * 8/2019 Swift ..................... A61B 1/015
10,512,519 B2 * 12/2019 Swift ................. A61B 1/00108
10,799,229 B2 * 10/2020 Swift ..................... A61B 90/35
2008/0262510 A1 * 10/2008 Clifford ................. A61N 1/306 604/501
2012/0041268 A1 * 2/2012 Grey ...................... A61B 1/267 600/199
2012/0059224 A1 * 3/2012 Wellen ................... A61B 1/227 600/200
2012/0083658 A1 * 4/2012 Hahn ................. A61B 17/0218 600/245
2012/0116170 A1 * 5/2012 Vayser ..................... A61B 1/07 600/245
2012/0327426 A1 * 12/2012 Hart ..................... A61B 5/1079 356/601
2014/0364695 A1 * 12/2014 Nadershahi ...... A61B 17/12136 600/219

(Continued)

*Primary Examiner* — Eduardo C Robert
*Assistant Examiner* — Steven J Cotroneo
(74) *Attorney, Agent, or Firm* — Quarles & Brady LLP

(57) ABSTRACT

An improved imaging ear speculum is disclosed. The speculum retains a small imaging module such as a camera near is distal opening. The imaging module is retained in a carrier, which is slid into a track or guide in an interior wall of the speculum. Improved specula may also include annular inflatable bladders arranged on their outside distal surface, which bladders can engage with the patient's ear and render the speculum selectively self-retaining.

5 Claims, 8 Drawing Sheets

(56) References Cited

U.S. PATENT DOCUMENTS

| | | | | |
|---|---|---|---|---|
| 2015/0351607 | A1* | 12/2015 | Ruppersberg | A61B 1/00193<br>600/473 |
| 2015/0374208 | A1* | 12/2015 | Ruppersberg | A61B 1/227<br>600/109 |
| 2018/0125345 | A1* | 5/2018 | Rebella | A61B 1/015 |
| 2020/0107714 | A1* | 4/2020 | Bar-Or | A61B 1/32 |
| 2022/0167841 | A1* | 6/2022 | Keogh | A61G 13/121 |
| 2024/0016377 | A1* | 1/2024 | Alleman | A61B 5/12 |

* cited by examiner

IMAGING SPECULUM FOR OTOLOGY

CROSS-REFERENCE TO RELATED APPLICATIONS

This patent application claims priority from and benefit of U.S. Provisional Patent Application 63/273,791, filed Oct. 29, 2021. The disclosure of the above-identified patent application is incorporated by reference herein.

FIELD OF THE INVENTION

Inventive embodiments related to ear speculums generally, and ear speculums incorporating electronic imaging components in particular.

BACKGROUND

Ear speculums are fundamental tools used in both otological examination and in procedures such as aural (neurotology) surgery. While most people are familiar with conical disposable office speculums that are used for visual otoscopes in a clinical setting, speculums are also important surgical tools. In surgery, as in examination, speculums are used to protect the sensitive ear canal from the passage of instruments and may be used as fulcra to assist in the positioning of such instruments, as described below. Thus, speculums and provide visual and mechanical access to inner ear structures.

A speculum is not a retractor. A speculum is not a cannula. Unlike a retractor, a speculum is generally not used in an incision, nor used to hold open tissue. One function of speculums used in otological surgery, for example, is to guide the operating instruments into the external ear canal and protect delicate tissues in the ear from advancing surgical tools. Speculums are generally controlled and held in position by the non-dominant hand or a clamp mechanism. In some cases, a self-retaining speculum uses expanding jaws to hold the speculum in place.

The speculum can also be used as a fulcrum where a surgical tool is rested on the edge of the speculum and moved or rotated about that point to do useful work. This is an advantage as the fulcrum is very close to the tissue and allows relatively large motion on the back side or proximal portion of the tool which translates that gross motion to the distal portion of the tool doing the fine motion. The ratio of tool lengths, distal and proximal, to the fulcrum creates a reduction of motion at the tool tip for the surgeon. This is useful as the surgical work in neuro-otology is often in the sub-millimeter range.

Speculums generally take the form of a truncated cone where the larger proximal opening and the smaller distal opening are nominally mutually parallel and orthogonal to a central axis. A single straight or tapering line can be swept 360 degrees around the axis connecting each opening to define the interior and exterior surfaces of the speculum, as shown below. The view and access through the speculum is from the larger opening (A) towards the smaller opening (B).

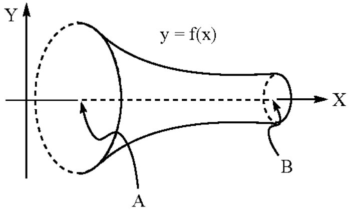

An operating speculum usually differs from the office speculum in that it is most often metal while the office device is usually plastic. This difference in materials permits a thinner wall thickness for the metal operating speculum. The distal openings of various sized operating speculums have a proportionally larger inner diameter, ID, when compared with the office speculums due to the difference in strengthen of materials.

An office speculum may have a handle attached with an illumination source, whereas the view through the operating speculum is illuminated via the source in the microscope, loupes or endoscope.

A variation of the above form is an endaural speculum which is similar in form to the above-mentioned speculum in shape but is split in two portions along the central axis. Each half is then attached or formed to one half of a joined handle. The joining mechanism of the handles creates a scissor like motion between the two handles to create and or maintain separation of the two speculum halves, or portions of the speculum. Alternatively, the speculum be separated into two portions and held by an adjustable mechanism so that the speculum is self-retaining in the ear canal. In this last case the joining mechanism can act as a tweezer where the physician can adjust a screw or the like and move the 2 halves of the speculum closer or further apart. These conventional speculums are described in additional detail below in relation to FIG. 1.

Conventionally, in the operating room, speculums are used in conjunction with microscopes or magnifiers worn by the surgeon (e.g., a loupe on the surgeon's to allow visualization within the ear canal or mastoid access. This arrangement relies on a direct line of sight from the magnifier and/or the surgeon's eye through the distal speculum aperture, and it places the magnification elements above the physician's hands and tools. An operating or surgical microscope is advantageous in that it permits the surgeon to use both hands during the procedure, by virtue of it being attached to a floor stand or wall mount. Likewise, loupes permit the use of both hands.

While microscope or loupe views of the ear canal through the speculum do not interfere with the workspace of the distal tip, their view can be blocked by the surgeon's hands or tools. Specifically, during the procedure, the surgeon's hands and tools can obscure the view into the speculum and ear canal or mastoid area, due to the hands and tools being between the imaging modality and the tissue of interest. Additionally, ergonomics can be an issue for the physician, who may wish to position themselves more comfortably for proper viewing, while still having effective control of their instruments. Moreover, in neither case can the surgeon see outside of the periphery of the distal opening of the speculum.

Endoscopes are an attempted solution to some of these issues. Endoscopes typically include small imaging systems located on the distal end of a flexible tube. An endoscope may include one or more ports which permit the insertion of instruments along the tube and parallel to the look axis of the imaging system. An endoscope may be inserted through an ear speculum to permit visualization of the ear canal. One advantage of endoscopes is that they permit the surgeon to see outside the margins of the distal opening of the speculums, which is to say, that the surgeon is capable of "looking around a corner," in a way they cannot do with microscopes and.

Endoscopes, however, have certain disadvantages in that they require the surgeon to use his/her non-dominant hand to position and hold the endoscope for viewing during the procedure, or have the hand of an assistant hold and position the endoscope. This is the "third hand" problem of endoscopic viewing. The endoscope occupies a hand which could be using tools in the case of a single surgeon. It further requires the surgeon to position their arm or shoulder in uncomfortable positions in order to direct the line of sight of the endoscope. Using an assistant presents direction of sight issues. The assistant may not intuitively know how to guide the endoscope or reposition the speculum for the benefit of the surgeon, and communication between the surgeon and the assistant may be imperfect leading to wasted time or errors.

Additionally, within the distal opening of the speculum, even a thin walled surgical speculum, there is little room to spare for the tip of the endoscope as even the smallest endoscopes are large in diameter when compared to the distal opening of the speculum.

Other problems exist with endoscopic viewing. The tip of the scope can be positioned for a wide field view of the inner ear canal but the balance of the endoscope shaft and body may interfere with tool use by the surgeon, as the shaft protrudes well out of the speculum into the space used by the surgeon's hands. So while the endoscope eliminates the obscuration problem of microscopes and loupes by virtue of the tip being "below the hands" of the physician there are still drawbacks.

U.S. Pat. No. 5,919,130A demonstrates these shortcomings of conventional endoscopic otoscopes. In that reference, a video otoscope is disclosed. The video otoscope includes a distal, insertable end around which is arranged a removable and disposable speculum. At the distal end of the insertable portion, the device has imaging optics arranged in what would otherwise be the distal aperture of a conventional speculum. The imaging optics form an image on an imager (i.e., at 2D array of detector elements), which sits along the centerline of what would otherwise be a conventional speculum. The device includes a transparent speculum portion, which surrounds the endoscopic components, and which is used for illumination with light originating from an annular array of optical fibers. While the device of U.S. Pat. No. 5,919,130A may be acceptable for examination, it has the same disadvantages shared by other endoscopes, namely, that the imaging components fill the space of the speculum and prevent the insertion of surgical tools.

Further improvement over conventional methods of illuminating and observing inner ear structures, while preserving space for manipulation of surgical tools, is required.

BRIEF SUMMARY

Inventive embodiments are directed to an imaging ear speculum useable for ear examination or surgery. In one aspect, the speculum has a proximal aperture and a distal aperture, where the distal aperture is smaller than the proximal aperture. The speculum has a circular cross section and may be defined by a surface of rotation about a central axis. In one embodiment, the speculum is a hollow truncated cone having an annular cross section.

In one aspect, the speculum has a track along an inner surface, which in certain embodiments may be an inwardly facing channel having an approximate square c-shaped cross section having mutually, inwardly projecting tabs. The channel may have an approximate square c-shaped cross section because it preferably matches the interior curvature of the speculum's inner surface, such that the back wall of the channel matches the curvature of the exterior of the speculum, and the inwardly projecting tabs match the curvature of the interior surface of the speculum. The channel or track may slidingly receive a carrier, which may be a flexible member having outwardly projecting wing portions that engage beneath the tabs of the speculum channel, such that the carrier may slide along the channel but is captured such that it cannot translate into the interior space circumscribed by the interior surface of the speculum. In addition to the outwardly projecting wing portions, the carrier may define a central, interior, tubular passage having open ends. That passage may slidingly receive a small imaging system, i.e., a camera assembly, which may have a circular cross section somewhere along its length such that it may slide along and within the interior tubular passage of the speculum, and may rotate within and with respect to the carrier. Thus, the camera may be inserted into the carrier, and then may be translated by motion of the carrier along the track from the proximal to the distal end of the speculum. The camera may also be rotated with respect to the carrier at any carrier position. A friction or interference fit between an exterior surface of the imaging system and the track, either or both of which may include a compressible and deformable material, retains the imaging system within the track without the need for manual support by the surgeon. The camera may have an optical power and position such that it may image objects placed at or near the distal aperture of the speculum.

In certain embodiments, the speculum has more than one internal track capable of carrying imaging systems. In certain embodiments, these tracks may be arranged at cardinal points around the interior surface of the speculum. In other embodiments, a pair of imaging systems may be arranged 180 degrees from one another (i.e., along a line bisecting a circular cross section of the inside of the speculum). Such embodiments may be useful for generating stereoscopic images of objects at or beyond the distal end of the speculum.

In certain embodiments, the speculum body is transparent, and the device includes an illumination source configured to illuminate objects near the distal end of the speculum through the speculum body. In other embodiments, the interior surface of the speculum includes additional tracks which carry illumination light sources.

Embodiments of the invention have certain advantages. By positioning an entire imaging system, including the imaging optics and the sensor, in a track that is located off of the center axis of the speculum, space is preserved within the speculum for surgical tools. When used with a self-retaining speculum, the imaging arrangement of inventive embodiments solves the "third hand" problem and provides a stable imaging platform that the surgeon does not need to hold.

Additional advantages will become evident upon consideration of the following detailed description.

BRIEF DESCRIPTION OF THE DRAWINGS

The present disclosure is illustrated by way of examples, embodiments and the like and is not limited by the accompanying figures, in which like reference numbers indicate similar, although in some cases not identical, elements. Elements in the figures are illustrated for simplicity and clarity and have not necessarily been drawn to scale. The figures along with the detailed description are incorporated and form part of the specification and serve to further illustrate examples, embodiments and the like, and explain various principles and advantages, in accordance with the present disclosure, where.

DETAILED DESCRIPTION

The described features, advantages, and characteristics may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus appearances of the phrase "in one embodiment," "in an embodiment," and similar language throughout this specification may, but do not necessarily, all refer to the same embodiment.

Figure 1:
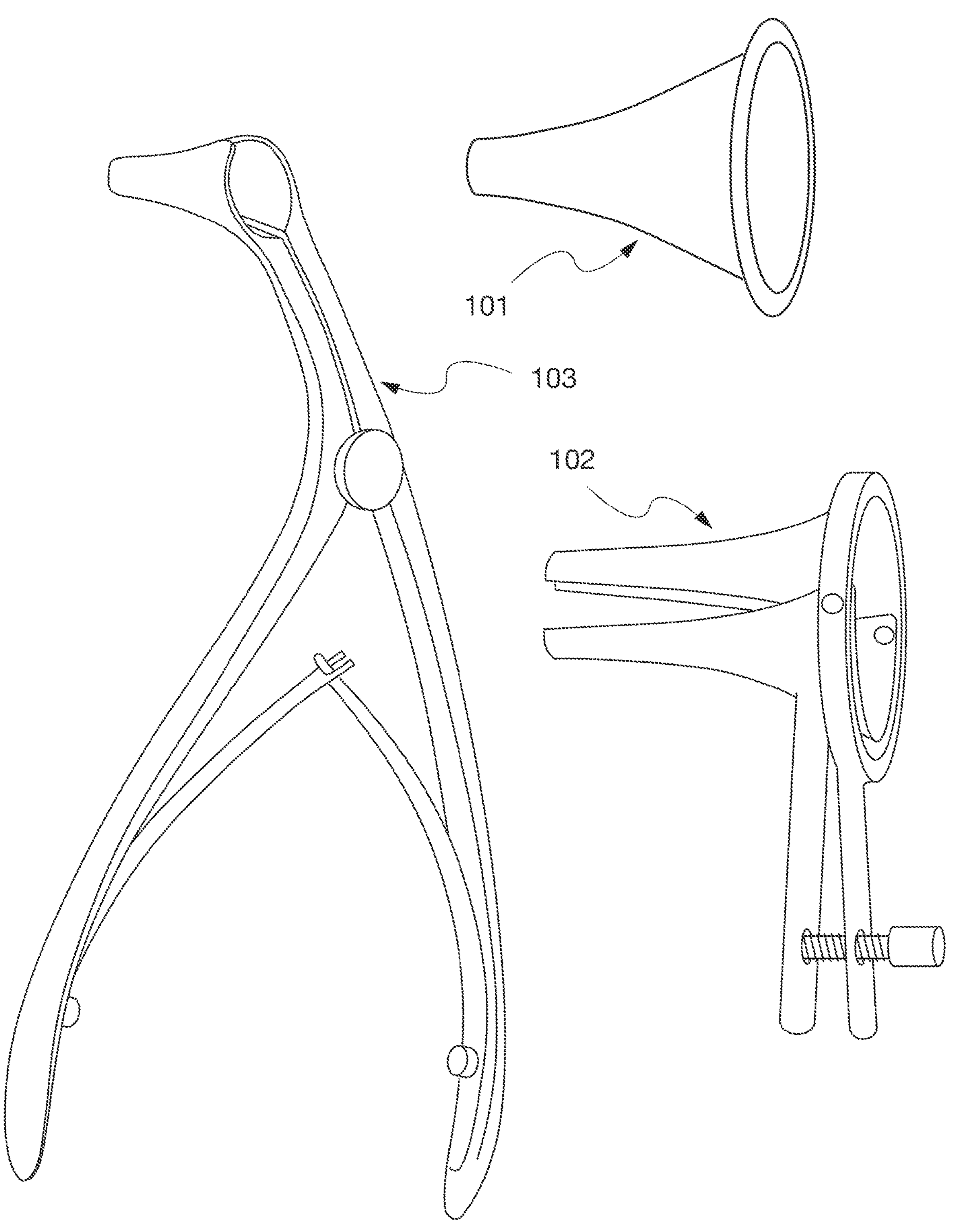
FIG. 1 shows a variety of conventional ear speculums.

Referring now to FIG. 1, there are shown a variety of conventional ear speculums, which are usable as surgical speculums. Conventional speculum 101 defines a proximal aperture and a smaller distal aperture, which conventionally are circular. The inside and outside surfaces of speculum 101 can be conceptualized as surfaces of rotation of a curve connecting the proximal and distal apertures rotated about a central mechanical axis of the speculum. Where the curve is a straight line, the speculum has the form of a hollow truncated cone having circular cross sections, but other connecting curves are usable. The rate at which the diameter of the outside surface of the speculum 101 expands with distance from the distal aperture is chosen to ensure that the speculum's outside diameter at a predetermined distance from the distal aperture exceeds a predetermined value. This ensures that the device cannot be inserted into the ear beyond a certain depth. Preferably, conventional speculum 101, and the inventive improvements made thereto described below, is a plastic or metal speculum through which a physician can examine or operate in the ear canal.

Referring still to FIG. 1, there is also shown an alternative conventional surgical speculum 102. Speculum 102 is a self-retaining speculum which can be placed in the ear and by means of a screw mechanism or otherwise be held in place freeing up one of the surgeon's hands. Speculum 103 is a Lembert type speculum which is a pliers like instrument which is operated with one hand and can permit a variable opening into the ear canal with which the physician can examine or operate. As with conventional speculum 101, conventional speculums 102 and 103 may be improved by application of the inventive embodiments, which will now be described.

Inventive embodiments are directed to improvements to speculums such as those discussed immediately above in reference to FIG. 1. As stated, a speculum may be approximated as a frustum of a cone formed as a revolution of continuous metal or other material. A physician or surgeon positions the speculum in the ear canal with the smaller opening (B) in the ear canal and the larger opening proximal (A). A speculum's shape can take the form of a portion of a circle or curve rotated around an axis analogous to the f(x) function shown above. The X axis in the figure shown above is the line of sight into the ear canal for the surgeon and the mechanical axis for the insertion of tools.

In certain embodiments, the interior sidewalls of the speculum contain formed guide slots, grooves, or other means, which direct the path of a miniature camera assembly towards the distal opening along the interior of the speculum in the direction of the axis of the speculum. This produces a slide-able track, allowing the camera to be positioned for best focus and field of view of relevant tissue, and allows it to be adjusted independently from the distal position of the speculum, which is most often held fixed relative to the anatomy.

Additional slots or guides in the direction of the speculum's mechanical central axis can independently or in communication with the camera's position allow illumination of fiber optics or LEDs to be directed towards the anatomical area of interest. Permitting the illumination to be adjusted distally and proximally along the central axis allows the illumination to cover the surgeon's work and or to minimize specular reflections or viewing by the camera of the tip of the illumination module(s). A distribution of the illumination module around or partially around the axis of the speculum can reduce shadowing in the image caused by tools in the field.

Additionally, the speculum itself can be made of a transparent material or contain a transparent layer (total internal reflection?) which permits the illumination to be directed towards the distal end of the speculum by total internal reflection within the body of the speculum, which may act as an optical waveguide for light emitted from an illumination source arranged at the proximal end of the speculum. Such an arrangement may reduce the intrusion on elements in distal opening by incorporating the speculum itself for illumination transport.

In certain embodiments, the surgeon can adjust the working distance of the imaging module by sliding the module in one or more openings or slits in the speculum following a parallel path of the axis of the speculum into which the imaging or imaging plus illumination elements are contained. By doing so the module moves closer or further away from the surgical site providing a change in working distance to the object of interest and the area seen. Such an opening along the axis of the speculum could permit the corresponding guides to be attached to the camera or illumination modules and slid along the edges of the opening. Or, the guides for motion could be features along the length of the opening(s) in the speculum. In some embodiments the slots are interruptions in the revolution of material about the axis. In some cases the slots are continuous from the proximal to distal ends.

In some embodiments, the speculum may contain Nitinol material, with its super-elastic properties, for a number of different effects. The Nitinol members in the sidewalls can grip the insert or the imaging or illumination module once positioned to maintain positioning or modify positioning of an insert, or module in communication with a control unit or by controls embedded on or near the speculum. Alternatively, the Nitinol can modify the shape of the exterior surface interfacing with tissue for better fitting, retention, or other.

The camera or imaging module described herein can be made inexpensively, to the point of being disposable, by use of wafer scale optics. This means that the imaging module's camera may be fabricated at the wafer level, with both the detector, associated detector microelectronics, and the imaging optics, fabricated at the wafer level, and the resulting wafer or wafers then being diced to singulate individual devices. Illumination modules can include LEDs with or without fiber optics or waveguides or micro or monolithic lens let arrays, or NA controlling means or combinations thereof. Display options for the signal generated by the detector are many including both direct view (i.e., direct view LCD or PDP monitors arranged on a pad, tablet or computer, wall mounted or on stands or brackets) or near-to-eye displays, such as glasses mounted or head mounted virtual microdisplays based on LCoS, micro-LEDs, scanning lasers or the like.

The imaging module and the illumination modules described above can be separate entities and their cross-sections can be different from that of an endoscope. The endoscope is a round narrow shaft wrapped in fiber optics to permit a symmetrically round rotatable cross section going into a body lumen or surgical opening or cannula. Because a goal of this device is to maximize the space available at the distal tip of the speculum the cross-section of the imaging and or illumination modules need not be rotationally symmetrical, as in the endoscope case, and can be flattened out to fit closely against the wall of the speculum to permit expanded space for tool access. This distribution of illumination around the interior walls of the speculum reduces shadowing. Alternatively, patterned illumination of the scene is possible by means of lensing, prisms, or holograms on or at the distal end of the illumination modules. In certain embodiments, scales or other fiducial markers may be projected by the speculum illumination system onto structures within the field of view of the camera system. Such patterned illumination can be useful in measurements and distance calculations. More than one illumination module can be used where the color temperature or wavelength ranges could be dissimilar for the purpose of depth measurements or other diagnostic purposes.

Due to the very small size of the imaging and illumination modules, in some cases 1 mm square in cross section, in some cases smaller or larger than 1 mm, they become difficult to position and manipulate by hand. U.S. Pat. No. 8,602,971, which is incorporated herein in its entirety, describes an imaging module or camera usable with the improvements described herein. As can be seen by review of that reference, the camera, though usefully small, has a round body (like an endoscope), and so cannot be easily manipulated with using a speculum. The inventive inserts described herein solve this problem. An inventive insert guides the insertion of the module and also serves as holder for the imaging modules. The insert has a non-rotationally symmetrical cross section, conforming to the speculum inner wall, and it performs a more useful means of holding and positioning the imaging and or illumination modules.

Figure 2:
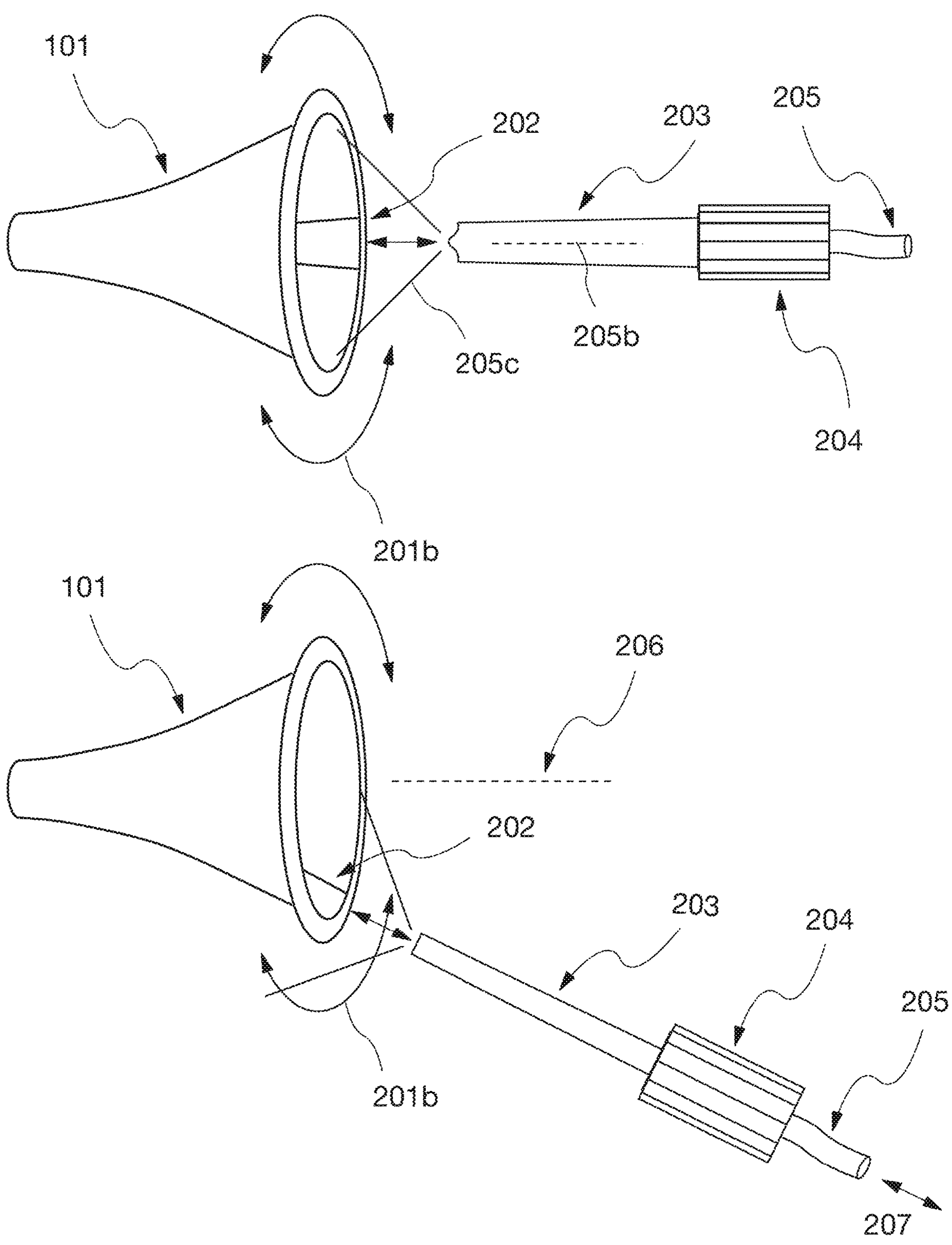
FIG. 2 shows an ear speculum assembly including an imaging system according to one embodiment.

Referring specifically now to FIG. 2, there is shown an improved speculum 101 according to an inventive embodiment. As in speculum 101 described in reference to FIG. 1, FIG. 2's speculum 101 includes a circular proximal aperture and a circular distal aperture, the edges of which are connected by a curve. The speculum is hollow and has interior and exterior surfaces that may be defined as surfaces of rotation about a central axis of curves (i.e., interior and exterior curves) connecting the apertures. The central axis may be a straight line through the centers of the proximal and distal apertures. Speculum 101 may include an annular rim or ledge near the proximal aperture as shown.

Speculum 101 includes additional elements such as a groove, guide, rails, or track 202, which is configured to receive and slidingly retain a carrier 203 which itself, carries an imaging module. In a preferred embodiment, track 202 has an approximately square c-shaped cross section and defines a recessed area beyond the interior surface of the speculum. In such embodiments, carrier 203 may have a pair of inwardly and mutually projecting short tabs that lie in what would otherwise be the interior surface of the speculum if it had a smooth, continuous interior surface. Carrier 203 slidingly proceeds along a path within the interior of the speculum, the path defined by guide structure 202. The mechanical axis or centerline of the speculum is shown as line 206 and the path of the guide 202 is offset from and angled with respect to axis 206. The speculum rotates within the ear canal shown by 101*b*. Therefore, the guide channels, 202, may occupy any rotational position along path 201*b* around the mechanical axis 206. Element 204 is a rotation collar or barrel enabling rotation of the imaging module 205 with respect to carrier 203. Imaging module 205 may include imaging optics, located at a distal end of the imaging module, an optical sensor or detector (not shown), and electrical wiring for transmitting sensor data to a non-illustrated control unit. The path of the electrical wiring (e.g., a cable) is shown at 207.

Preferably, carrier 203 is formed of a conformable material such as plastic or elastomeric plastic and is sized and shaped to slidingly engage features of the rail or track 202. Preferably, carrier 203 makes a friction fit with the track 202 such that carrier 203 is supported in track 202 but requires pressure to advance it along track 202. In cases where track 202 has an approximate square c-shaped cross section, carrier 203 may have outwardly projecting wings or tab portions configured to be captured behind the inwardly projecting tabs of the track 202, such that the carrier 203 cannot fall into the interior volume defined by the interior surface of the speculum. Preferably, carrier 203 is hollow and defines an open cylindrical through passage along axis 205B. The imaging module 205 is preferably cylindrical, or includes a cylindrical housing or exterior surface, and fits within the through passage of the carrier, and is sized to be retained therein by a friction fit or the like. Imaging module 205 may be rotated with respect to carrier 203 (and therefore also with respect to speculum 202) by rotational actuation of element 204, which may be a knurled barrel that is rigidly attached to the imaging module 205. Element 204 may also define a stop position of imaging module While the example of FIG. 2 includes tracks or guides 202 within the wall of the speculum itself, this is not a requirement. In other embodiments the speculum is a continuously walled speculum of metal or plastic, which contains an insert conforming to the interior geometry of the speculum. The insert may include the slide mounts (i.e., guide tracks) receiving the imaging and illumination modules in the insert versus the slides being in the speculum in the previous embodiment. In such embodiments, the insert has the functionality in direction of view, position of distal image and illumination tip of the first embodiment.

Figure 3:
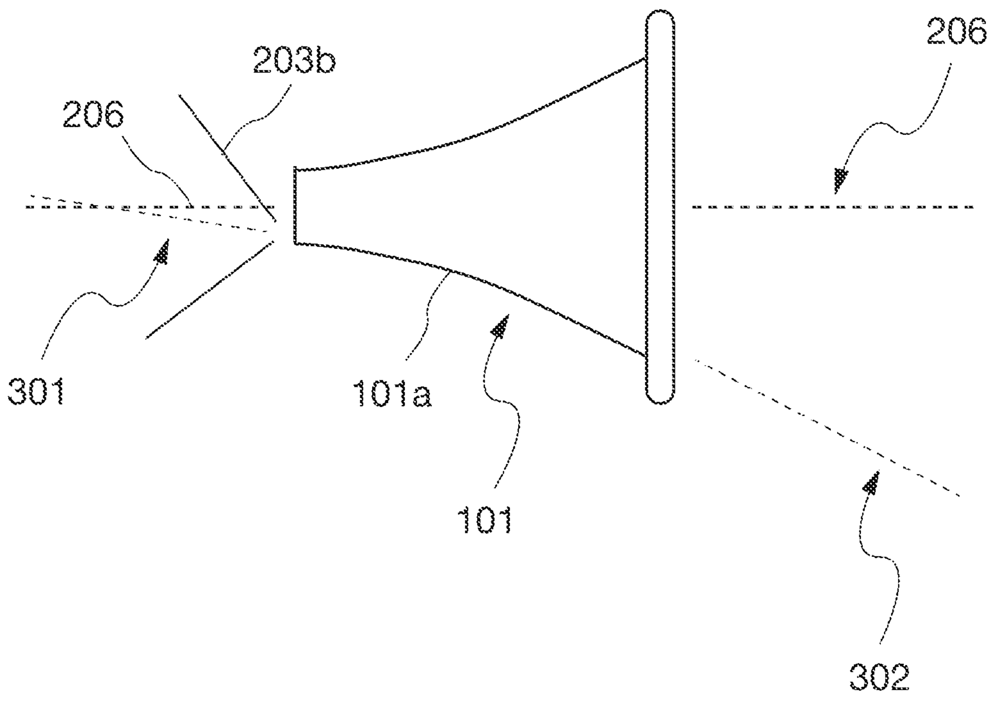
FIG. 3 shows a side view of the speculum assembly of FIG. 2.
Figure 3:
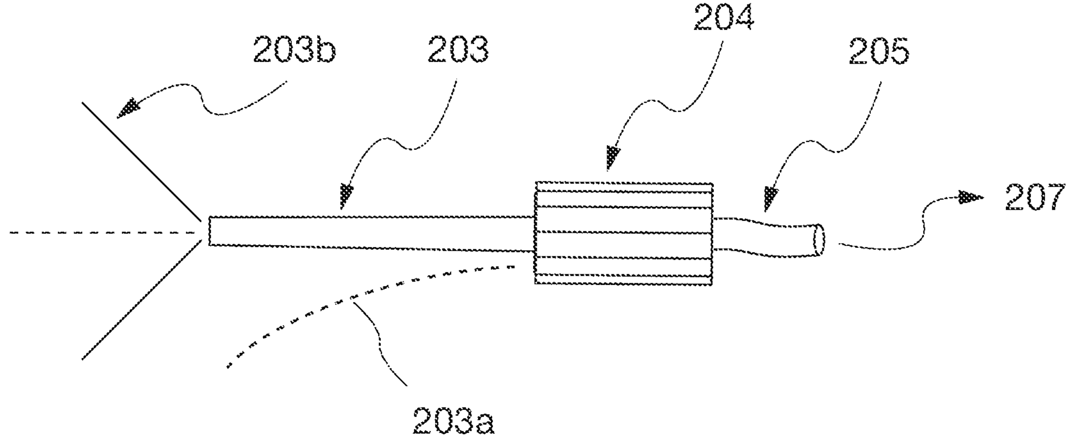

Referring now to FIG. 3, there is shown an arrangement between imaging module 205, carrier 203 and speculum 101 in additional detail. Specifically, FIG. 3, in its upper portion, shows a side view of speculum 101 having a mechanical centerline axis 206.

Guides, channel, rails or a track (which are not visible in FIG. 3 as they are on the interior surface of speculum 101), follow a path 101*a* which is typically not a straight line but a function as described hereinabove (i.e., along a curve connecting the distal and proximal apertures of the speculum). Preferably, this path 101*a* will follow the curve of the interior surface of the speculum from the proximal aperture to the distal aperture, which surface will generally be parallel to the exterior surface of the speculum when the device is of uniform thickness. The imaging module 205 and the guide 203 may be malleable or compliant and can be deflected as shown by a curve, 203*a*. 203*b*, the field of view of the imaging module is then redirected by this path as shown by 302 the proximal end of path and 301 the distal path. Due to the path described by 101*a* the line of sight of the imaging module is slightly oblique with reference to the mechanical axis 206.

As can be seen in FIG. 3, the speculum and camera assembly share the general direction of their respective axes (206,301), however the camera's look angle is position-able at an angle relative to the speculum axis. This enables a view beyond the distal lip of the speculum. By rotating the speculum and camera assembly other views beyond the distal lip of the speculum can be realized. This enables a view like an endoscope but without requiring the third hand or the body of the endoscope interfering with the surgeon's hand and tool access.

Figure 4:
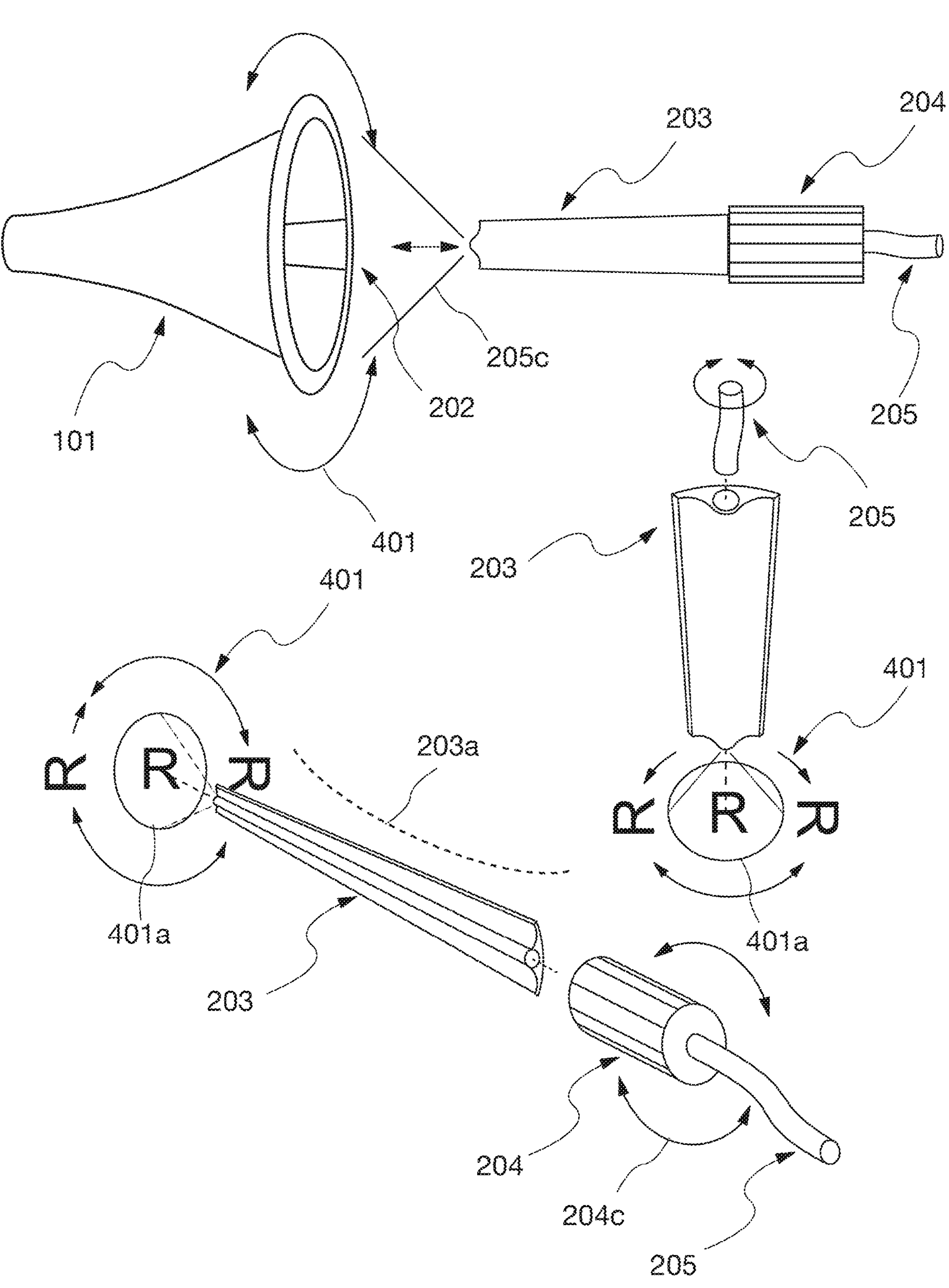
FIG. 4 shows a imaging module and guide usable with the assembly of FIG. 2.

FIG. 4 shows the interfaces between guide 203, imaging module 205 and speculum 101 in additional detail. As can be seen, guide 203 may include transverse tabs or wings along either side of its central axis, which wings allow guide 203 to be slotted into and slidingly captured by guide channel 202. The adjustment ring or barrel, 204, permits the imaging module 205 to be physically rotated, 204*c*, within the guide, 203. This will rotate an image formed by the imaging optics of the imaging module 203 with respect to the module's sensor, and will in turn rotate a displayed image 401*a* electronically communicated from the sensor to a display device, which rotates the displayed image 401*a* to a desired orientation. 203*a* shows that the imaging module can be flexed by the path 202 and still permit rotation of the imaging module. Such a feature may be useful in allowing adjustment of the imaging module 205's look angle, which will be discussed further below in reference to FIG. 8.

Figure 5:
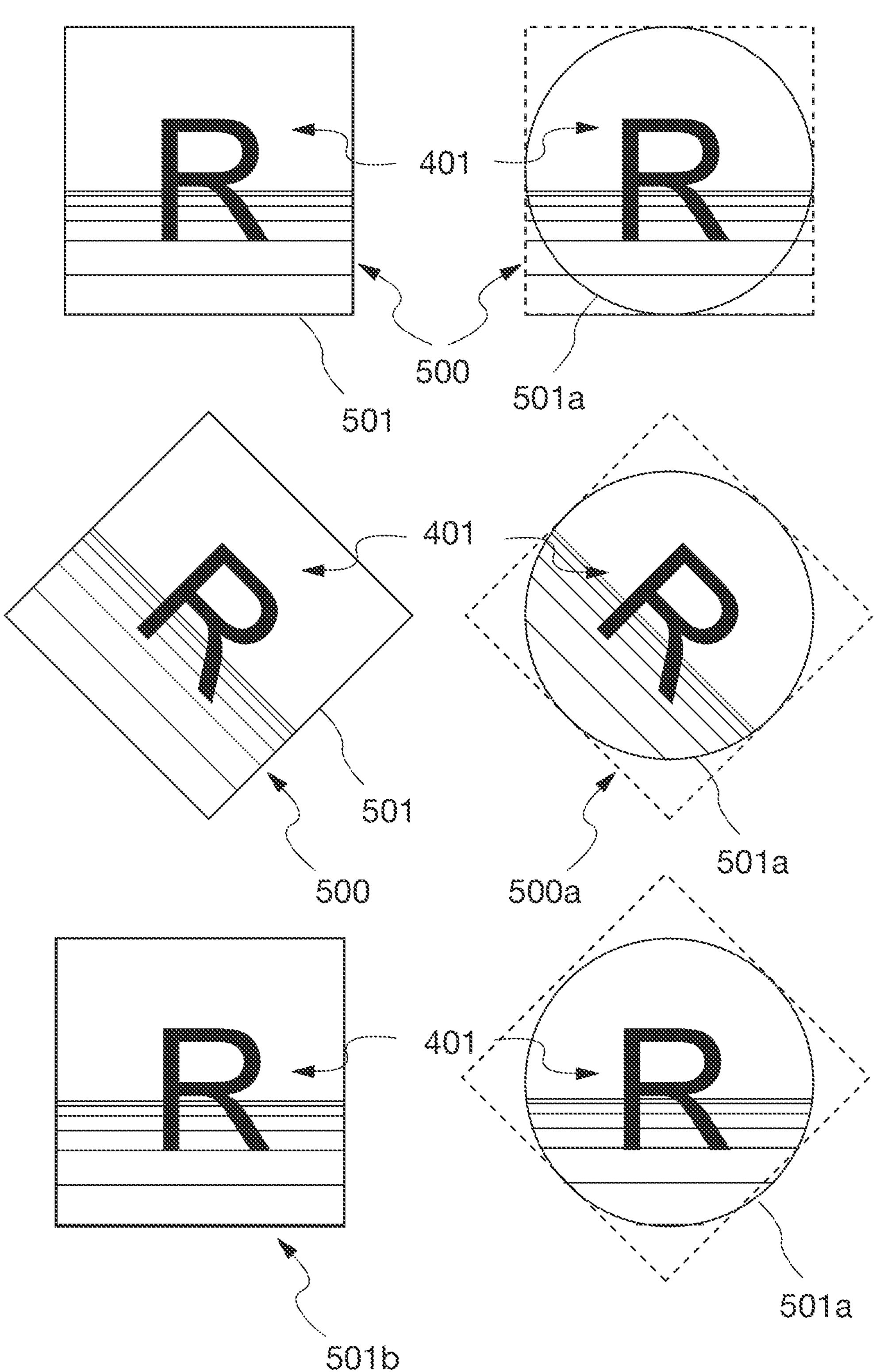
FIG. 5 schematically illustrates the use of imaging speculums according to some embodiments to define a horizon line.

FIG. 5 shows a combination of 3 elements in 2 configurations. The first element, the sensor, 500 produces an image from the pixels within the wafer scale optics camera assemblies, which make up the imaging module, and is most often rectangular, and is most often square. The sensor produces a rectangular, and most often a square output, 501 on the display. The second element is a mask, 501 for a square mask, often proportional to the sensor, or a circular mask, 501*a* which produces a circular image from the pixels inscribed within the circular mask. When a square output is desired the mask, 501 is equivalent to the sensor. The circular image, 501*a* has a subset of the total number of pixels on the sensor. The circular mask is most often produced by the electronic control unit, but a physical mask in the nature of a field stop in close proximity to the sensor of the imaging module 205, or an internal image plane, is within the scope of the invention. The object being viewed, 401, is the third element. It has an orientation and horizon. The horizon is the same horizon the physician sees as she/he looks at the surgical site. The R and L eye line of the Doctor defines a line and the horizon in the scene is parallel to that line when there is no rotation. Most often a line can be drawn between the physician's right and left hand. A comfortable working posture can be found when the horizon of the surgical site on the display, the horizon of the image, and the line between hands, are all more or less parallel to the horizon described by the R and L eye. But, anatomical and surgical consideration often dictate or make it advantageous to rotate the position of the imaging module to a new position. As the imaging module is contained within the speculum rotating the speculum can produce a slightly different view; due to the slightly oblique viewing angle of the module follows along the interior of the speculum. To reorient the horizon requires the square mask system to physically rotate within the speculum as shown in earlier figures. With a circular mask the imaging module need not be rotated physically but rotated electronically in the control module. Having done so, the square sensor orientation is hidden from view. In the case of stereo imaging modules they could have square or circular masks but would preferably physically rotate like the square mono configuration to keep the horizon parallel to that of the physician.

Figure 6:
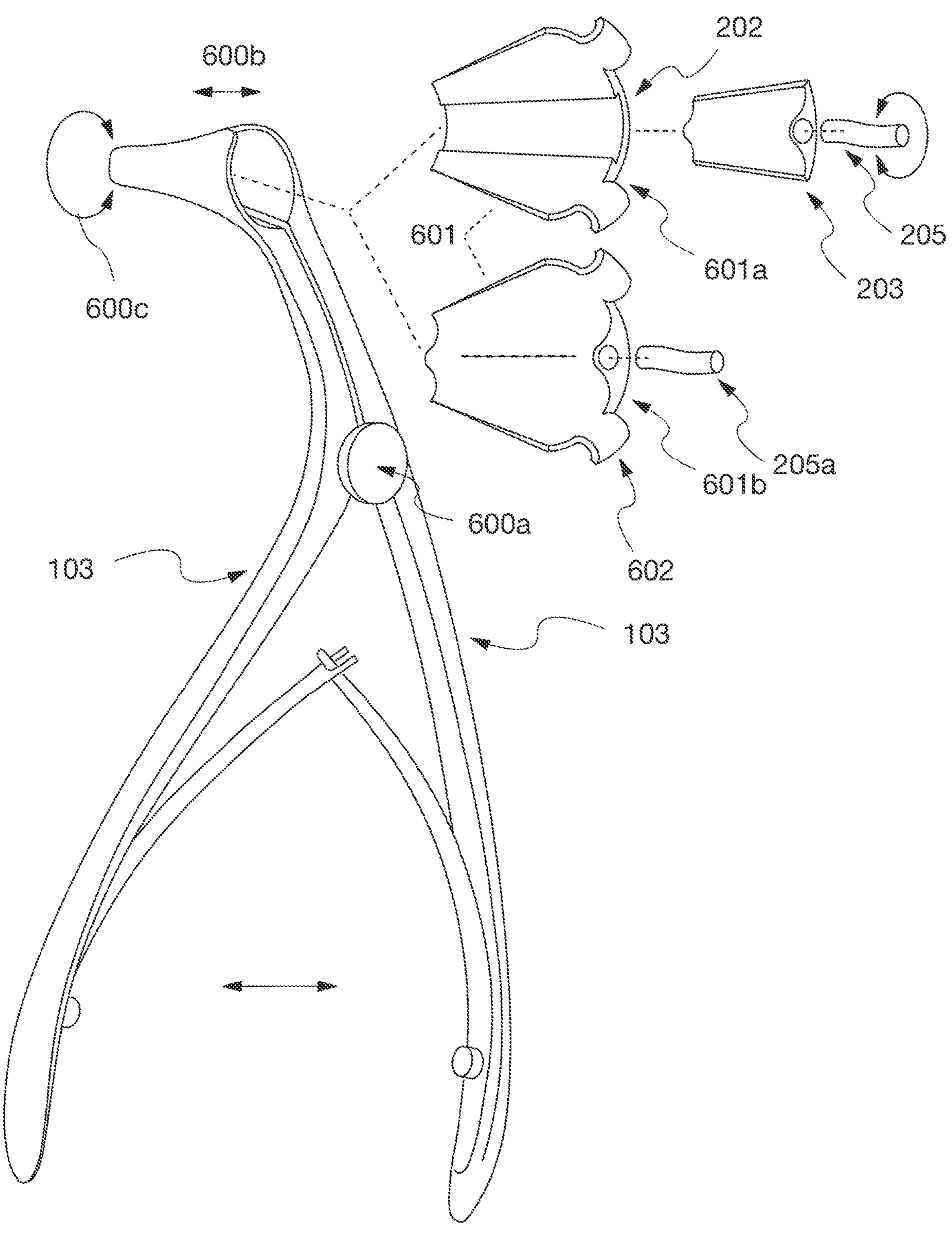
FIG. 6 shows an alternative speculum according to one embodiment.

FIG. 6 shows another embodiment of an improved imaging speculum. The speculum 103 of FIG. 6 is a Lembert style speculum. This speculum is a plier type with a central pin, 600*a*, which is closer to the distal end rather than the proximal end. The distal portion opens and closes a smaller amount that the proximal end which is scaled for the human hand. When the distal jaws open or close, shown by 600*b*, the interior opening of the speculum changes size. A speculum insert, 601, for the imaging module is made to attach to one or both sides of the distal jaws. The speculum insert may be disposable. In a preferred embodiment, speculum insert 601 is made of multiple portions, for example, a first half carrying an imaging module (601*a*, 601*b*), and a second, mating half, which is not illustrated in FIG. 6 for clarity. The half inserts are attached to speculum 103 with integrated clips, as shown in 602. The example insert of 601*a* is usable with a guide 203 and a rotatable image module, 205. As in the embodiments above, the speculum insert includes a channel or track 202 for sliding receipt of the guide 203. The example insert of 601*b* does not require a guide 202 and is usable with an imaging module with a circular mask. In this case, channel 202 and guide 203 are not necessary, and imaging module 205*a* is captured directly by insert 601*b* by passing imaging module 205 through an aperture or the like as shown, sized to create a tight friction fit with module 205*a*. A similar 2-part insert system could be used with the self-retaining speculum 102 in FIG. 1, or any of the other embodiments described above.

More generally, in cases of a split speculum, such as the endaural speculum or self-retaining speculum, where there are functionally two halves, the inserts may be made as a pair of inserts each inserted, retained by, or held by the speculum halves. The inserts could contain the aforementioned elements. The speculum can be made of metal while the disposable portions are of plastic or differing material. Various configurations of surface finishes and color can be chosen to minimize scattered and stray light.

Further embodiments of the invention are directed to inclusion of an inflatable cuff which encircles the outer distal wall of the speculum. This makes the speculum selectively self-retaining function such that the surgeon or assistant isn't required to hold or position the speculum. By using one or more inflatable annular bladder, damage to thin soft tissue overlying bony external auditory canal structures is prevented. Unlike an elastomer or rigid speculum, the pressure per unit area can be adjustable to a safe, effectively self-retaining level from a console or control unit by means of a communicating tube or channel between the cuff and the control unit. The control unit can continually monitor pressures and or other biometric data of the patient which is controlled, displayed, or otherwise communicated to or by the surgeon. There are many shape and size variations of the external auditory canal and the cuff will conform to all shapes without pressure points. In certain embodiments, the inflatable cuff is a single inflatable member encircling the speculum. In alternative embodiments, it is made from multiple inflatable chambers. Because the air pressure should be monitored to enable safe pressure levels against soft tissue, the air pressure line to the console or control unit should be integral between the speculum cuff and control means.

A further embodiment involves separating the air line from the speculum to the control unit permitting an intermediate module containing pump and pressure monitoring means which then communicates to a main control or console via an electrical wire or wirelessly. The module could then be mounted close to the surgical site.

In some cases, the inflatable cuff and tubing would be disposable for sterility reasons and reduction of bio-burden.

Figure 7:
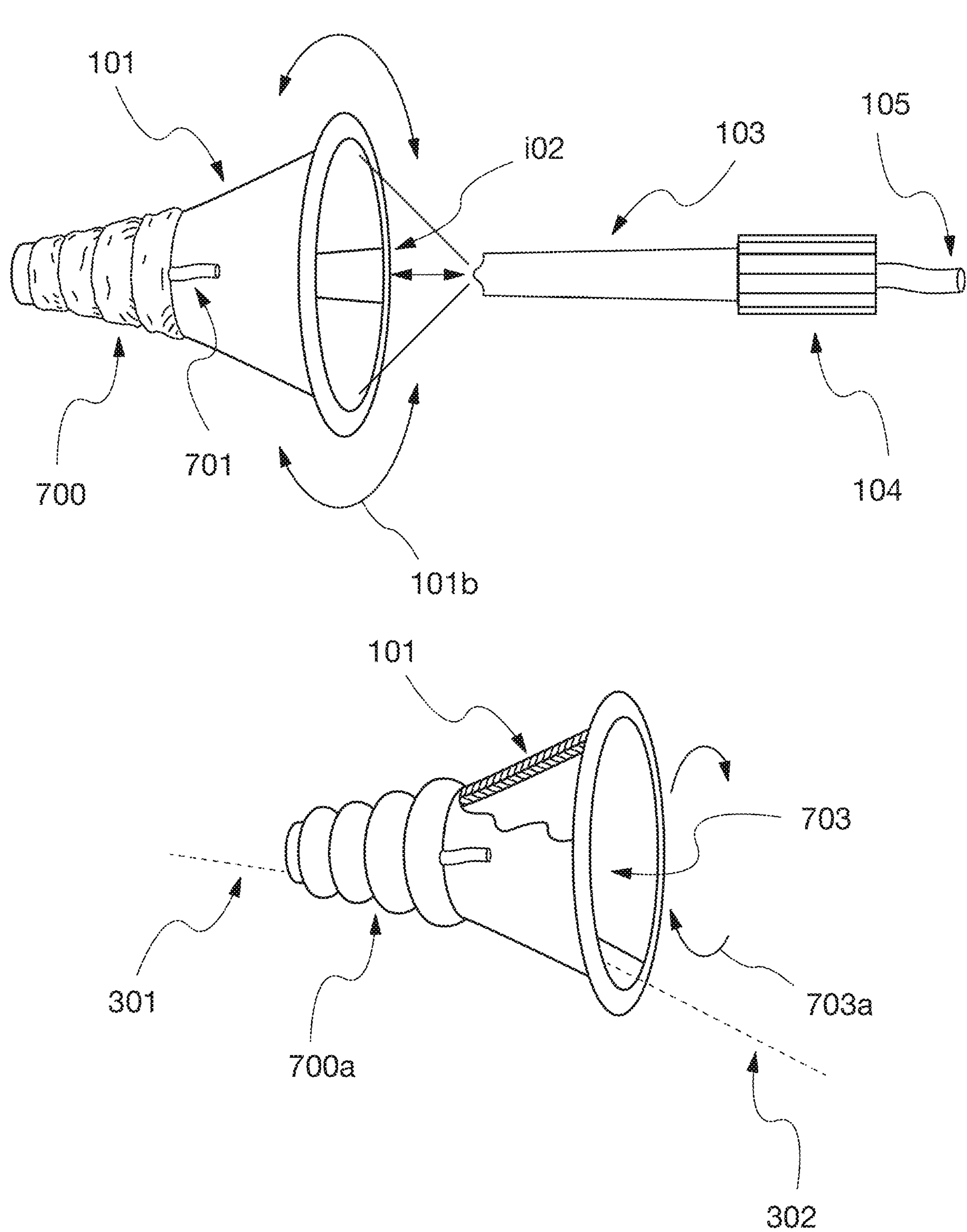
FIG. 7 shows an alternative speculum according to another embodiment.

FIG. 7 shows an exemplary embodiment including an inflatable cuff of the aforementioned type. The speculum 101 of FIG. 7 is similar to the speculums set forth above in that it has a track, guide or other structure 102 configured for slidingly engaging a guide 103 including an imaging module 105. However, the speculum 101 of FIG. 7 includes one or more inflatable annular bladders (700, 700*a*) arranged annularly around a distal region of speculum 101. Bladders 700, 700*b* permit a speculum having a circular or otherwise smooth perimeter cross section (e.g., an ovoid, ellipse, or any other shape to which bladders 700 can seal) to be self-retaining. The assembly is pictured with the bladders in their deflated state (700) as well as in their inflated state (700*b*). Bladders may be inflated and deflated by means of fluid communication with a tubular assembly (701) which connects the bladders to an unillustrated control unit having a reversible pump.

In one embodiment, bladders 700 are fixed and sealed to an exterior surface of speculum 101. In an alternative embodiment, bladders 700 are arranged on an exterior surface of a collar or shell configured to slip over the distal end of speculum 101 and mate with an exterior surface of speculum 101. In such embodiments, the collar or shell will have an internal surface that is slightly bigger than the exterior surface of the speculum, such that the two surfaces are in surface contact. In such embodiments, the two parts may be held together by friction. In other embodiments, the collar or shell may be pinned against the speculum by inwardly directed pressure created by the inflated bladders pushing on the interior surface of the patient's ear canal. In other embodiments, a mechanical fastening means joins the distal and proximal parts of the speculum, for example, tabs, pins, ridges or other means of frictionally or mechanically joining the two parts. In yet other embodiments, the speculum 101 includes a proximal section and a distal section, the distal section carrying the bladders 700 on its exterior surface. In such embodiments, the distal section of the speculum may be rotatable with respect to the proximal section, through a rotational interface such as a collar or the like. Arrangements permitting the speculum, or at least a proximal section of the speculum, to rotate with respect to the bladders are useful in that they provide some ability to rotate the image of the square output configuration imaging module, at least for small angles. In embodiments where the interior of the speculum contains a channel (102, 202), the imaging module may rotate within the outer layer of the speculum as shown in the cut-away.

In another aspect, a speculum according to the invention includes a pneumatic cuff mechanism, controls, pump, tubing or other portions to control the position of the tip of the imaging module or illumination modules, directing and holding them, together or independently, in a position to direct their line of sight to an object of interest. The imaging and illumination modules can be made of flexible and or compliant materials which can be deflected by air pressure from the inflating and monitoring means. This requires the cuff, control unit, and optional intermediate unit to be multifunctional, having now a self-retaining function, a tip deflecting function, and biometric data collection.

A further embodiment relates to the multifunctional control means of the preceding paragraph. A pneumatic communication means may be directed into the insert retaining the imaging module from the pump and control unit to a bladder of inflatable portion of the insert which when pressurized deflects a portion of the insert which then changes the line of sight of the imaging module contained within the insert. The insert would contain a flexible member which when pressure is released returns the imaging module line of sight to its nominal position. Flexible endoscopes use wires and springs to push or pull the endoscope tip to change its line of sight. The disadvantage of such a mechanical means is when the tip is deflected by a tool used by the surgeon the tip does not necessarily return to is previous or nominal position. The advantage of pneumatic control is its compliant to rigid and back to compliant properties. This same mechanism could be used to direction of fiber optic or LED illumination modules. Alternatively, a Nitinol wire mechanism could steer one or both types of modules.

A multi-axis gyro can placed on but not in the speculum, an exterior positioning preserves the interior of the speculum for viewing and tool use. The gyro can communicate to the control unit and detect orientation changes. The viewing orientation can be linked and controlled utilizing this feedback.

Figure 8:
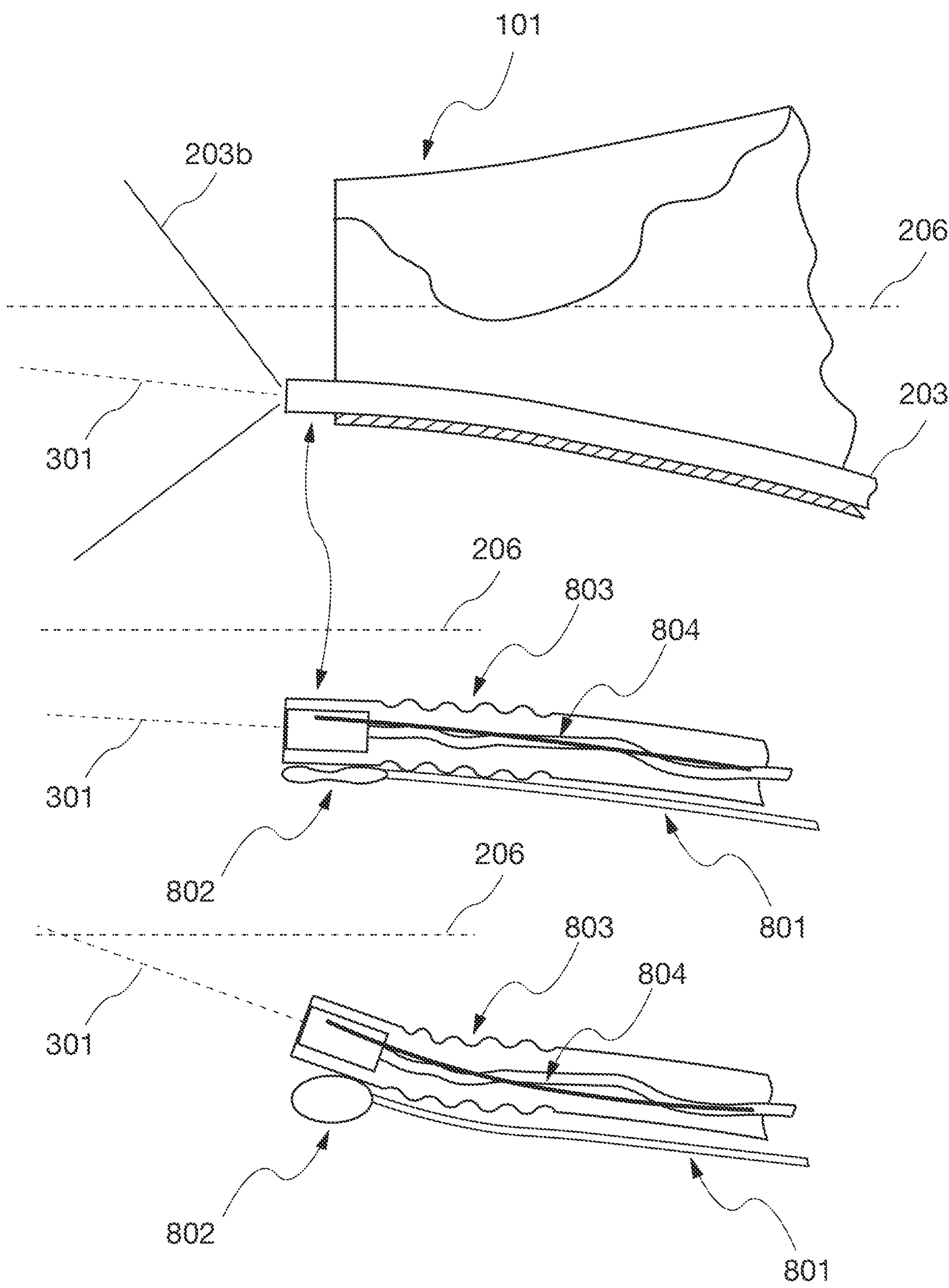
FIG. 8 shows an arrangement for adjusting the look angle of a speculum imaging system according to an embodiment.

FIG. 8 shows an example of one of the embodiments described immediately above, which is usable to improve any of the aforementioned speculums described in this Specification. In the embodiment of FIG. 8, guide 203 carrying an imaging module, or specifically, a distal end of an imaging module, may be angularly deflected in order to adjust the look angle 301, and therefore, the center of the field of view 203*b* of the imaging module. As can be seen in the upper portion of FIG. 8, a speculum 801 has arranged, along an interior surface, a guide 203. Guide 203, at its distal end, carries an imaging module (e.g., a camera assembly having imaging optics, a detector, and a cable as shown). The camera has a look angle 301 (i.e., the center of the sensor's field of view) and a field of view 203*b*.

Because of the interior surface shape of speculum 101, the look angle of the imaging module 301 will tend to be slightly non-zero with respect to the mechanical central axis (i.e., the axis of rotational symmetry) of speculum 101, and will tend to be inclined slightly toward that axis. Thus, the look angle 301 tends to be approximately (but not entirely) parallel to the mechanical axis 206 of the speculum. The default look angle of imaging module may be biased in any predetermined matter by pre-bending flexible member 804, which may be a stiff wire or the like.

In certain cases, however, the default look angle of the imaging module 301 may not be suitable, and the surgeon may want to adjust it. To provide for angular adjustment of the guide 203, an inflatable structure (e.g, a bladder) 802 is provided at a distal end of the speculum 801. The guide also includes a flexible region 803. The bladder 802 may be inflated, deflecting the distal end of guide 203, and changing the look angle of imaging module 301. When the bladder is deflated, guide 203 returns to its nominal position by operation of flexible member 804 (e.g., a stiff wire). Inflatable structure 802 may be inflated and deflated by applying positive or negative pneumatic pressure to the bladder through a pneumatic communication means 801 (i.e., a tube), connected to a control unit having a reversible pump.

Although the example of FIG. 8 shows the bladder 802 located below the distal end of guide 202 and past the distal end of speculum 101, these are not requirements. In alternative embodiments, additional bladders may located above, and/or on one or both lateral sides of the distal end of the guide 203. Bladders may be located beyond the distal end of the speculum as shown or may be attached to the interior speculum walls at the distal end of speculum.

The exemplary structures disclosed herein are for illustrative purposes and are not to be construed as limiting. In addition, variations and modifications can be made on the aforementioned structures without departing from the concepts of the present invention and such concepts are intended to be covered by the following claims unless these claims by their language expressly state otherwise.

What is claimed is:

1. An ear speculum system, comprising:

a speculum having a distal rim defining a distal aperture, a proximal rim defining a proximal aperture, a central axis passing through a center of the distal and proximal apertures, and a body having an inner and an outer surface, the body connecting the distal and proximal apertures, wherein the inner surface defines a track extending from the proximal aperture along the inner surface to the distal aperture;

wherein the system comprises a carrier slidingly received in the track, the carrier having a proximal end and a distal end and includes a central portion defining a hollow through passage having a closed inner surface extending from the proximal end to the distal end, an imaging system being slidingly captured within the through passage of the carrier;

wherein the carrier further comprises a first and second flattened wing portions arranged on either side of the central portion, the wing portions being curved to define a curved concave surface facing the central axis when the carrier is received in the track.

2. The speculum system of claim 1, further including a barrel attached to the imaging system configured for rotating the imaging system with respect to the carrier.

3. The speculum system of claim 1, wherein the speculum includes a first of said tracks including the imaging system slidingly engaged in the first track, and a second of said tracks including an illumination system slidingly engaged in the second track.

4. The speculum system of claim 1, wherein the body is split into at least two mating halves, which together, define a perimeter surface arranged about said axis.

5. The speculum system of claim 1, further including an inflatable bladder arranged proximal to the distal aperture and on one side of a distal end of the imaging system, the inflatable bladder configured to, in an inflated state, bend the distal end of the imaging system relative to a proximal end of the imaging system so as to alter a look angle of the imaging system.

* * * * *